United States Patent
Okamoto et al.

(10) Patent No.: US 10,519,083 B2
(45) Date of Patent: Dec. 31, 2019

(54) METHOD FOR PRODUCING TRANS-1-CHLORO-3,3,3-TRIFLUOROPROPENE

(71) Applicant: Central Glass Company, Limited, Ube-shi, Yamaguchi (JP)

(72) Inventors: Satoru Okamoto, Kawagoe (JP); Koji Ueda, Kawagoe (JP); Takamasa Kitamoto, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 16/070,090

(22) PCT Filed: Jan. 12, 2017

(86) PCT No.: PCT/JP2017/000707
§ 371 (c)(1),
(2) Date: Jul. 13, 2018

(87) PCT Pub. No.: WO2017/122703
PCT Pub. Date: Jul. 20, 2017

(65) Prior Publication Data
US 2019/0031583 A1 Jan. 31, 2019

(30) Foreign Application Priority Data
Jan. 15, 2016 (JP) ................. 2016-006652

(51) Int. Cl.
*C07C 17/20* (2006.01)
*C07C 17/25* (2006.01)
(Continued)

(52) U.S. Cl.
CPC ............ *C07C 17/206* (2013.01); *B01J 27/08* (2013.01); *C07C 17/25* (2013.01); *C07C 21/18* (2013.01);
(Continued)

(58) Field of Classification Search
CPC ............................ C07C 17/25; C07C 17/206
See application file for complete search history.

(56) References Cited

U.S. PATENT DOCUMENTS 5,811,603 A * 9/1998 Elsheikh ................. C07C 17/00
570/166
6,018,084 A 1/2000 Nakada et al.
(Continued)

FOREIGN PATENT DOCUMENTS

EP 2 341 040 A1 7/2011
JP 9-183740 A 7/1997
(Continued)

OTHER PUBLICATIONS

International Search Report (PCT/ISA/210) issued in PCT Application No. PCT/JP2017/000707 dated Mar. 21, 2017 with English translation (four (4) pages).
(Continued)

*Primary Examiner* — Medhanit W Bahta
(74) *Attorney, Agent, or Firm* — Crowell & Moring LLP (57) ABSTRACT

The present invention provides a method for efficiently producing 1-chloro-3,3,3-trifluoropropene from a low-reactivity intermediate product. More specifically, provided is a method for producing trans-1-chloro-3,3,3-trifluoropropene, characterized by reacting a halogenated $C_3$ hydrocarbon compound represented by the following general formula (1) with hydrogen fluoride in a gas phase in the presence of a solid catalyst and chlorine $$C_3H_XCl_YF_Z \quad (1)$$

wherein X is 2 or 3; when X=2, Y is an integer of 1 to 4, Z is an integer of 0 to 3, and Y+Z=4; and, when X=3, Y is an integer of 1 to 5, Z is an integer of 0 to 4, and Y+Z=5;
(Continued)

provided that the general formula (1) represents any halogenated $C_3$ hydrocarbon compound other than trans-1-chloro-3,3,3-trifluoropropene.

23 Claims, 2 Drawing Sheets

(51) Int. Cl.
*C07C 21/18* (2006.01)
*B01J 27/08* (2006.01)
C07B 61/00 (2006.01)
C07C 17/38 (2006.01)

(52) U.S. Cl.
CPC ........ *B01J 2523/31* (2013.01); *B01J 2523/47* (2013.01); *B01J 2523/67* (2013.01); *B01J 2523/68* (2013.01); *B01J 2523/84* (2013.01); *C07B 61/00* (2013.01); *C07C 17/38* (2013.01)

(56) References Cited

U.S. PATENT DOCUMENTS

| | | |
|---|---|---|
| 2005/0033097 A1 | 2/2005 | Tung et al. |
| 2011/0172472 A1 | 7/2011 | Sakyu et al. |
| 2011/0224465 A1 | 9/2011 | Merkel et al. |
| 2012/0172636 A1 | 7/2012 | Pokrovski et al. |
| 2013/0211154 A1* | 8/2013 | Cottrell .................. C07C 17/25 570/155 |
| 2014/0005446 A1 | 1/2014 | Imura et al. |
| 2016/0002128 A1 | 1/2016 | Pokrovski et al. |
| 2016/0332936 A1* | 11/2016 | Wang ...................... C07C 17/25 |
| 2017/0113986 A1 | 4/2017 | Okamoto et al. |
| 2017/0217860 A1 | 8/2017 | Karube et al. |

FOREIGN PATENT DOCUMENTS

| | | | |
|---|---|---|---|
| JP | 11-180908 A | 7/1999 | |
| JP | 2007-501843 A1 | 2/2007 | |
| JP | 2013-522196 A | 6/2013 | |
| JP | 2014-28802 A | 2/2014 | |
| JP | 2014-509310 A | 4/2014 | |
| WO | WO-2015126584 A1 * | 8/2015 | ............. C07C 17/10 |
| WO | WO 2016/009946 A1 | 1/2016 | |
| WO | WO 2016/056602 A1 | 4/2016 | |

OTHER PUBLICATIONS

Japanese-language Written Opinion (PCT/ISA/237) issued in PCT Application No. PCT/JP2017/000707 dated Mar. 21, 2017 (four (4) pages).
Extended European Search Report issued in counterpart European Application No. 17738457.5 dated Aug. 21, 2019 (seven pages).

* cited by examiner

METHOD FOR PRODUCING TRANS-1-CHLORO-3,3,3-TRIFLUOROPROPENE

FIELD OF THE INVENTION

The present invention relates to a method for producing trans-1-chloro-3,3,3-trifluoropropene from a halogenated $C_3$ hydrocarbon compound.

BACKGROUND ART

It is known that trans-1-chloro-3,3,3-trifluoropropene (for which the abbreviation is 1233zd(E)) is a compound usable as low-global-warming-potential (GWP), next-generation polyurethane foaming agents, working fluids, coolants etc.

In general, 1-chloro-3,3,3-trifluoropropene (abbreviated as 1233zd) is produced by fluorination of 1,1,1,3,3-pentafluoropropane (abbreviated as 240fa) or 1,1,3,3-tetrachloro-2-propene (abbreviated as 1230za) with hydrogen fluoride in the presence of a fluorination catalyst. The fluorination is carried out in a gas-phase or liquid-phase reaction system. The liquid-phase fluorination reaction is generally performed under pressurized conditions.

For example, Patent Document 1 discloses a method for producing 1-chloro-3,3,3-trifluoropropene (1233zd) by reacting 1,1,1,3,3-pentachloropropane (240fa) with hydrogen fluoride in a gas phase in the presence of a solid fluorination catalyst. Patent Document 2 discloses a method for producing 1-chloro-3,3,3-trifluoropropene (1233zd) by reacting 1,1,1,3,3-pentachloropropane (240fa) with hydrogen fluoride in the absence of a catalyst. Patent Document 3 discloses a method for producing 1-chloro-3,3,3-trifluoropropene (1233zd) by reacting 1,1,1,3,3-pentachloropropane (240fa) in a liquid phase in the presence of a Lewis acid catalyst or a mixture thereof within a reaction vessel at a temperature lower than 150° C., continuously extracting hydrogen chloride and 1-chloro-3,3,3-trifluoropepene (1233zd) generated in the reaction vessel, and then, isolating 1-chloro-3,3,3-trifluoropepene (1233zd).

PRIOR ART DOCUMENTS

Patent Documents

Patent Document 1: Japanese Laid-Open Patent Publication No. H09-183740
Patent Document 2: Japanese Laid-Open Patent Publication No. H11-180908
Patent Document 3: Japanese Laid-Open Patent Publication (Translation of International Publication) No. 2007-501843

SUMMARY OF THE INVENTION

In the case where 1-chloro-3,3,3-trifluoropropene (1233zd) is produced by fluorination of 1,1,1,3,3-pentachloropropane (240fa) with hydrogen fluoride by the method of Patent Document 1, the fluorination proceeds as an equilibrium reaction depending on the partial pressures of hydrogen fluoride and hydrogen chloride. The thus-obtained reaction product contains not only 1-chloro-3,3,3-trifluoropropene (1233zd), but also more fluorinated products such as 1,1,1,3,3-pentafluoropropane (abbreviated as 245fa) and less fluorinated products such as 1,1,3,3-tetrachloro-1-fluoropropane (abbreviated as 241fa) and 1,3,3-trichloro-1,1-difluoropropane (abbreviated as 242fa). In particular, 1,3,3-trichloro-1,1-difluoropropane (242fa) is formed as an intermediate product during the non-catalytic liquid-phase fluorination reaction of 240fa to 1233zd. However, the reaction rate of the fluorination reaction is significantly low so that the intermediate product becomes accumulated in the reaction vessel to cause a deterioration in productivity.

In the case where 1233zd and/or 1,3,3,3-tetrafluoropropene (abbreviated as 1234ze) is produced by non-catalytic gas-phase fluorination reaction of 240fa by the method of Patent Document 2, the fluorination reaction needs to be performed by heating for a long time at a high temperature.

The present invention has been made to solve the above problems. It is an object of the present invention to provide a method for efficiently producing trans-1-chloro-3,3,3-trifluoropropene from a low-reactivity intermediate product.

The present inventors have found as a result of extensive researches that, even though a halogenated hydrocarbon compound such as 1,3,3-trichloro-1,1-difluoropropane formed during the non-catalytic liquid-phase fluorination reaction of 1,1,1,3,3-pentachloropropane is very low in reactivity, it is possible to efficiently produce trans-1-chloro-3,3,3-trifluoropropene by heating such a halogenated hydrocarbon compound along with chlorine and hydrogen fluoride in a gas phase in the presence of a solid catalyst, and have consequently accomplished a production method of trans-1-chloro-3,3,3-trifluoropropene according to the present invention.

The present applicant has found that it is possible to produce trans-1-chloro-3,3,3-trifluoropropene by reacting a halogenated $C_3$ hydrocarbon compound represented by the following general formula (1) with hydrogen fluoride in a gas phase in the presence of chlorine, and have already filed a patent application (PCT/JP2015/069784) based on such a finding.

$$C_3H_XCl_YF_Z \qquad (1)$$

In the general formula (1), X is 2 or 3; when X=2, Y is an integer of 1 to 4, Z is an integer of 0 to 3, and Y+Z=4; and, when X=3, Y is an integer of 1 to 5, Z is an integer of 0 to 4, and Y+Z=5; provided that the general formula (1) represents any halogenated $C_3$ hydrocarbon compound other than trans-1-chloro-3,3,3-trifluoropropene.

In the patent application PCT/JP2015/069784, each of working examples discloses "non-catalytic reaction" without the use of a solid catalyst.

The present inventors have recently found that the above fluorination reaction proceeds favorably even in the presence of a solid catalyst. The present application has been filed based this finding.

Namely, it is possible in the present invention to improve the productivity of trans-1-chloro-3,3,3-trifluoropropene by extracting an intermediate product accumulated in a reactor and efficiently converting the intermediate product to trans-1-chloro-3,3,3-trifluoropropene through solid-catalytic gas-phase fluorination reaction in the presence of chlorine.

The present invention includes the following inventive aspects.

[Inventive Aspect 1]

A production method of trans-1-chloro-3,3,3-trifluoropropene, comprising reacting a halogenated $C_3$ hydrocarbon compound represented by the following general formula (1) with hydrogen fluoride in a gas phase in the presence of a solid catalyst and chlorine.

$$C_3H_XCl_YF_Z \qquad (1)$$

In the general formula (1), X is 2 or 3; when X=2, Y is an integer of 1 to 4, Z is an integer of 0 to 3, and Y+Z=4; and, when X=3, Y is an integer of 1 to 5, Z is an integer of 0 to 4, and Y+Z=5; provided that the general formula (1) represents any halogenated $C_3$ hydrocarbon compound other than trans-1-chloro-3,3,3-trifluoropropene.

[Inventive Aspect 2]

The production method according to Inventive Aspect 1, wherein the solid catalyst is a metal fluoride containing at least one kind of metal selected from the group consisting of aluminum, chromium, titanium, manganese, iron, nickel, cobalt, copper, magnesium, zirconium, molybdenum, zinc, tin, lanthanum, niobium, tantalum and antimony.

[Inventive Aspect 3]

The production method according to Inventive Aspect 1 or 2, wherein, in the reacting, a $C_3$ hydrocarbon compound represented by the following general formula (2) is added and reacted with hydrogen fluoride in a gas phase in the presence of chloride.

$$C_3H_VF_W \tag{2}$$

In the general formula (2), when V+W=8, V is an integer of 0 to 8; when V+W=6, V is an integer of 0 to 6; and, when V+W=4, V is an integer of 0 to 4.

[Inventive Aspect 4]

The production method according to Inventive Aspect 1 or 2, wherein the halogenated $C_3$ hydrocarbon compound is at least one selected from the group consisting of 1,1,1,3,3-pentachloropropane (240fa), 1,1,3,3-tetrachloropropene (1230za), 1,3,3,3-tetrachloropropane (1230zd), 1,1,3,3-tetrachloro-1-fluoropropane (241fa), 1,1,1,3-tetrachloro-3-fluoropropane (241fb), 1,3,3-trichloro-3-fluoropropene (1231zd), 1,3,3-trichloro-1-fluoropropene (1231zb), 3,3,3-trichloro-1-fluoropropene (1231ze), 1,1,3-trichloro-3-fluoropropene (1231za), 1,3,3-trichloro-1,1-difluoropropane (242fa), 1,1,3-trichloro-1,3-difluoropropane (242fb), 1,1,1-trichloro-3,3-difluoropropane, 1,3-dichloro-3,3-difluoropropene (1232zd), 3,3-dichloro-1,3-difluoropropene (1232ze), 3,3-dichloro-1,1-difluoropropene (1232zc), 1,3-dichloro-1,3-difluoropropene (1232zb), 1,1-dichloro-3,3-difluoropropane (1232za), cis-1-chloro-3,3,3-trifluoropropene (1233zd (Z)), 3-chloro-1,1,3-trifluoropropene (1233zc), 3-chloro-1,3,3-trifluoropropene (1233ze), 1-chloro-1,3,3-trifluoropropene (1233zb), 3,3-dichloro-1,1,1-trifluoropropane (243fa), 1,3-dichloro-1,1,3-trifluoropropane (243fb), 1,1-dichloro-1,3,3-trifluoropropane (243fc), 1-chloro-1,1,3,3-tetrafluoropropane (244fb) and 3-chloro-1,1,1,3-tetrafluoropropane (244fa).

[Inventive Aspect 5]

The production method according to Inventive Aspect 1 or 2, wherein the reacting is performed at a temperature of 100° C. to 400° C.

[Inventive Aspect 6]

A production method of trans-1-chloro-3,3,3-trifluoropropene, comprising reacting at least one halogenated hydrocarbon compound selected from the group consisting of 1,1,3,3-tetrachloro-1-fluoropropane (241fa), 1,1,1,3,3-pentachloropropane (240fa) and 1,3,3-trichloro-1,1-difluoropropane (242fa) with hydrogen fluoride at a temperature of 100° C. to 400° C. in a gas phase in the presence of a solid catalyst and chlorine.

[Inventive Aspect 7]

The production method according to Inventive Aspect 6, wherein, in the reacting, a $C_3$ hydrocarbon compound represented by the following general formula (2) is added and reacted.

$$C_3H_VF_W \tag{2}$$

In the general formula (2), when V+W=8, V is an integer of 0 to 8; when V+W=6, V is an integer of 0 to 6; and, when V+W=4, V is an integer of 0 to 4.

[Inventive Aspect 8]

A production method of trans-1-chloro-3,3,3-trifluoropropene, comprising the following steps:

(A) reacting 1,1,1,3,3-pentachloropropane (240fa) with hydrogen fluoride, thereby obtaining an intermediate product;

(B) forming trans-1-chloro-3,3,3-trifluoropropene by reacting the intermediate product obtained in the step (A) with hydrogen fluoride at a temperature of 100° C. to 400° C. in a gas phase in the presence of a solid catalyst and chlorine.

[Inventive Aspect 9]

The production method according to Inventive Aspect 8, wherein, in the step (B), the reacting is performed in the presence of a $C_3$ hydrocarbon compound represented by the following general formula (2).

$$C_3H_VF_W \tag{2}$$

In the general formula (2), when V+W=8, V is an integer of 0 to 8; when V+W=6, V is an integer of 0 to 6; and, when V+W=4, V is an integer of 0 to 4.

[Inventive Aspect 10]

The production method according to Inventive Aspect 8, wherein, in the step (A), the reacting is performed in a liquid phase in the absence of a catalyst, and wherein the production method further comprises:

recovering, from the step (A), a reaction product gas containing trans-1-chloro-3,3,3-trifluoropropene and a reaction liquid; and using, in the step (B), the intermediate product contained in the reaction liquid.

[Inventive Aspect 11]

The production method according to Inventive Aspect 10, wherein the 1,1,1,3,3-pentachloropropane and the hydrogen fluoride are continuously or intermittently introduced into the step (A), and wherein the reaction product gas and the reaction liquid are continuously or intermittently recovered.

[Inventive Aspect 12]

The production method according to Inventive Aspect 8, wherein the intermediate product is at least one selected from the group consisting of 1,1,3,3-tetrachloro-1-fluoropropane (241fa), 1,1,1,3-tetrachloro-3-fluoropropane (241fb), 1,3,3-trichloro-3-fluoropropene (1231zd), 1,3,3-trichloro-1-fluoropropene (1231zb), 3,3,3-trichloro-1-fluoropropene (1231ze), 1,1,3-trichloro-3-fluoropropene (1231za), 1,3,3-trichloro-1,1-difluoropropane (242fa), 1,1,3-trichloro-1,3-difluoropropane (242fb), 1,3-dichloro-3,3-difluoropropene (1232zd), 3,3-dichloro-1,3-difluoropropene (1232ze), 3,3-dichloro-1,1-difluoropropene (1232zc), 1,3-dichloro-1,3-difluoropropene (1232zb), cis-1-chloro-3,3,3-trifluoropropene (1233zd(Z)), 3,3-dichloro-1,1,1-trifluoropropane (243fa), 1,3-dichloro-1,1,3-trifluoropropane (243fb), 1,1-dichloro-1,3,3-trifluoropropane (243fc), 1-chloro-1,1,3,3-tetrafluoropropane (244fb) and 3-chloro-1,1,1,3-tetrafluoropropane (244fa).

[Inventive Aspect 13]

The production method according to Inventive Aspect 8, wherein the intermediate product contains at least 1,3,3-trichloro-1,1-difluoropropane (242fa).

[Inventive Aspect 14]

The production method according to Inventive Aspect 8, wherein, in the step (B), the reacting is performed at a temperature of 150° C. to 300° C.

[Inventive Aspect 15]

The production method according to Inventive Aspect 8, further comprising recovering and using an unreacted fraction of the intermediate product in the step (B).

[Inventive Aspect 16]

The production method according to Inventive Aspect 8, wherein cis-1-chloro-3,3,3-trifluoropropene is formed along with the trans-1-chloro-3,3,3-trifluoropropene in the step (B).

[Inventive Aspect 17]

The production method according to Inventive Aspect 16, wherein the cis-1-chloro-3,3,3-trifluoropropene is used in the step (B).

[Inventive Aspect 18]

The production method according to Inventive Aspect 16, further comprising converting the cis-1-chloro-3,3,3-trifluoropropene to trans-1-chloro-3,3,3-trifluoropropene by heating at a temperature of 100° C. to 400° C.

EFFECTS OF THE INVENTION

In the production method of trans-1-chloro-3,3,3-trifluoropropene according to the present invention, the intermediate product of very low reactivity such as 1,3,3-trichloro-1,1-difluoropropane formed during the non-catalytic liquid-phase fluorination reaction of 1,1,1,3,3-pentachloropropane is heated along with chlorine and hydrogen fluoride in a gas phase in the presence of the solid catalyst. It is possible in this method to prevent a decrease of catalytic activity and efficiently produce trans-1-chloro-3,3,3-trifluoropropene.

When the fluorination of a halogenated hydrocarbon compound with a high boiling point, in particular a halogenated hydrocarbon compound with a high chlorination degree, is ordinarily performed in a gas phase in the presence of a solid catalyst, the yield of trans-1-chloro-3,3,3-trifluoropropene may be decreased with decrease in the activity of the catalyst due to the generation of a tar product etc. (see the after-mentioned comparative example 1). It is however possible to significantly suppress a decrease of catalytic activity and achieve stable production of trans-1-chloro-3,3,3-trifluoropropene by performing this catalytic fluorination reaction in the presence of chlorine.

BRIEF DESCRIPTION OF DRAWINGS

FIG. 2 is a graph showing changes in the results of gas chromatography analysis of a reaction product obtained in Example 5 with the progress of reaction time. In FIG. 2, the term "1233E yield (%)" refers to the concentration (GC area %) of 1233E in the reaction product.

FIG. 3 is a graph showing changes in the results of gas chromatography analysis of a reaction product obtained in Example 6 with the progress of reaction time. In FIG. 3, the term "1233E yield (%)" refers to the concentration (GC area %) of 1233E in the reaction product.

DETAILED DESCRIPTION OF EMBODIMENTS

The present invention is embodied as, but is not limited to, a method for efficiently producing trans-1-chloro-3,3,3-trifluoropropene (1233zd(E)) from an intermediate product of very low reactivity such as 1,3,3-trichloro-1,1-difluoropropane (242fa) formed during the non-catalytic liquid-phase fluorination reaction of 1,1,1,3,3-pentachloropropane (240fa). The present invention is directed to a method for producing trans-1-chloro-3,3,3-trifluoropropene by reacting a halogenated $C_3$ hydrocarbon compound as a raw material with hydrogen fluoride in the presence of a solid catalyst and chlorine.

The halogenated $C_3$ hydrocarbon compound used as the raw material in the present invention is a halogenated $C_3$ hydrocarbon compound represented by the following general formula (1).

$$C_3H_XCl_YF_Z \qquad (1)$$

In the general formula (1), X is 2 or 3; when X=2, Y is an integer of 1 to 4, Z is an integer of 0 to 3, and Y+Z=4; and, when X=3, Y is an integer of 1 to 5, Z is an integer of 0 to 4, and Y+Z=5; provided that the general formula (1) represents any halogenated $C_3$ hydrocarbon compound other than trans-1-chloro-3,3,3-trifluoropropene.

Examples of the halogenated $C_3$ hydrocarbon compound represented by the general formula (1) are: when X=2, $C_3H_2Cl_1F_3$, $C_3H_2Cl_2F_2$, $C_3H_2Cl_3F_1$ and $C_3H_2Cl_4$; and, when X=3, $C_3H_3Cl_1F_4$, $C_3H_3Cl2F3$, $C_3H_3Cl_3F_2$, $C_3H_3Cl_4F_1$ and $C_3H_3Cl_5$.

The halogenated $C_3$ hydrocarbon compound used as the raw material in the present invention is preferably at least one selected from the group consisting of 1,1,3,3-tetrachloro-1-fluoropropane (241fa), 1,1,1,3-tetrachloro-3-fluoropropane (241fb), 1,3,3-trichloro-3-fluoropropene (1231zd), 1,3,3-trichloro-1-fluoropropene (1231zb), 3,3,3-trichloro-1-fluoropropene (1231ze), 1,1,3-trichloro-3-fluoropropene (1231za), 1,3,3-trichloro-1,1-difluoropropane (242fa), 1,1,3-trichloro-1,3-difluoropropane (242fb), 1,3-dichloro-3,3-difluoropropene (1232zd), 3,3-dichloro-1,3-difluoropropene (1232ze), 3,3-dichloro-1,1-difluoropropene (1232zc), 1,3-dichloro-1,3-difluoropropene (1232zb), cis-1-chloro-3,3,3-trifluoropropene (1233zd(Z)), 3,3-dichloro-1,1,1-trifluoropropane (243fa), 1,3-dichloro-1,1,3-trifluoropropane (243fb), 1,1-dichloro-1,3,3-trifluoropropane (243fc), 1-chloro-1,1,3,3-tetrafluoropropane (244fb) and 3-chloro-1,1,1,3-tetrafluoropropane (244fa).

In the case where the fluorination reaction of 1,1,1,3,3-pentachloropropane is performed in a liquid phase in the absence of a catalyst, the resulting reaction liquid contains a trace amount of trans-1-chloro-3,3,3-trifluoropropene. However, the conversion reaction from trans-1-chloro-3,3,3-trifluoropropene to trans-1-chloro-3,3,3-trifluoropropene itself does not serve as a production method and thus is excluded in the present specification.

A $C_3$ hydrocarbon compound can be used together with the halogenated $C_3$ hydrocarbon compound as the raw reaction material in the present invention. As a result of the effect of a chlorine source such as hydrogen chloride or chlorine radical generated from the halogenated hydrocarbon compound during the production process, the $C_3$ hydrocarbon compound is also converted to trans-1-chloro-3,3,3-trifluoropropene. The $C_3$ hydrocarbon compound used herein is a compound represented by the following general formula (2).

$$C_3H_VF_W \qquad (2)$$

In the general formula (2), when V+W=8, V is an integer of 0 to 8; when V+W=6, V is an integer of 0 to 6; and, when V+W=4, V is an integer of 0 to 4.

Examples of the $C_3$ hydrocarbon compound represented by the general formula (2) are: when V+W=8, $C_3F_8$, $C_3H_1F_7$, $C_3H_2F_6$, $C_3H_3F_5$, $C_3H_4F_4$, $C_3H_5F_3$, $C_3H_6F_2$, $C_3H_7F_2$ and $C_3H_8$; when V+W=6, $C_3F_6$, $C_3H_1F_5$, $C_3H_2F_4$, $C_3H_3F_3$, $C_3H_4F_2$, $C_3H_5F_1$ and $C_3H_6$; and, when V+W=4, $C_3F_4$, $C_3H_1F_3$, $C_3H_2F_2$, $C_3H_3F_1$ and $C_3H_4$.

More specifically, there can be used 1,1,1,3,3-pentafluoropropane (245fa), trans-1,3,3,3-tetrafluoropropene (1234ze (E)), cis-1,3,3,3-tetrafluoropropene (1234ze(Z)), 1,1,3,3-tetrafluoropropene (1234zc), 3,3,3-trifluoropropine or the like as the $C_3$ hydrocarbon compound.

The halogenated $C_3$ hydrocarbon compound as the raw material is not limited to a reaction product of the non-catalytic liquid-phase fluorination reaction of 1,1,1,3,3-pentachloropropane (240fa), and can be formed by any method. For example, it is feasible to form this raw material compound by fluorinating 1,1,1,3,3-pentachloropropane with hydrogen fluoride at 250° C. through a fluorinated chromium oxide catalyst (see Japanese Laid-Open Patent Publication No. H09-183740) or by reacting 1,1,1,3,3-pentachloropropane with hydrogen fluoride in a liquid phase for 5 hours at 200° C. under 100 kg/cm$^2$ (about 10 MPa) (see Japanese Laid-Open Patent Publication No. H11-180908).

[Solid Catalyst]

As disclosed by the present applicant in the patent application PCT/JP2015/069784, the fluorination reaction of the present invention (i.e., the conversion reaction of the halogenated $C_3$ hydrocarbon compound represented by the general formula (1) to trans-1-chloro-3,3,3-trifluoropropene) proceeds in a gas phase in the presence of chlorine even without the use of a solid catalyst. On the other hand, the present inventors have recently found a tendency that the use of a solid catalyst leads to a higher yield of 1233E at the same temperature whereby it is possible by the use of a solid catalyst to, even at a lower temperature, achieve the same level of 1233 yield as that achieved at a higher temperature by the use of no catalyst. The fluorination reaction of the present invention, in which the coexistence of chlorine gas is essential, may cause a load on reactor. It is accordingly of great technical significance to decrease the reaction temperature with the use of the solid catalyst. Hereinafter, the solid catalyst will be explained in detail below.

The solid catalyst used in the present invention can be any catalyst capable of promoting the formation of trans-1-chloro-3,3,3-trifluoropropene by contact of the halogenated $C_3$ hydrocarbon compound with hydrogen fluoride through the catalyst in a gas phase in the presence of chlorine A commonly known solid catalyst (heterogeneous catalyst) is widely usable.

Specific examples of the solid catalyst usable in the present invention are metal compounds (such as metal oxide, metal fluoride, partially fluorinated metal oxide, metal complex and the like) and activated carbons.

Among others, a metal compound catalyst is preferred. Particularly preferred are a metal oxide, a metal fluoride and a partially fluorinated metal oxide (also simply referred to as "fluorinated metal oxide").

As the fluorination reaction of the present invention proceeds in a gas phase in the presence of the metal oxide as the solid catalyst, the metal oxide is gradually fluorinated by contact with HF. More specifically, when HF is fed into the reactor filled with the metal oxide such as alumina or chromia as the solid catalyst, an oxygen atom of the metal oxide is gradually substituted with fluorine so as to form a so-called "partially fluorinated metal oxide (suitably typified by "fluorinated alumina" and "fluorinated chromia")". As the fluorination further proceeds, the metal oxide turns into a "metal fluoride" in which all oxygen has been substituted with fluorine. The solid catalyst used in the present invention can be any of "metal oxide", "metal fluoride" and "partially fluorinated metal oxide (fluorinated metal oxide)".

In the present invention, however, the catalytic activity of the "metal oxide" is often more stable in the case where the reaction is performed after once feeding a predetermined amount of HF through the metal oxide at a predetermined temperature than in the case where the reaction is performed immediately after the filling of the metal oxide. Consequently, "partially fluorinated metal oxide (fluorinated metal oxide)" formed in the system (by contact with HF) is considered as a particularly preferable example of the solid catalyst in the present invention.

There is no particular limitation on the kind of the metal contained in the metal compound. The metal contained in the metal compound is preferably at least one kind selected from the group consisting of aluminum, chromium, manganese, zirconium, titanium and magnesium. The metal compound may contain one kind of metal solely or two or more kinds of metals in combination.

In the case of using two or more kinds of metals in combination, it is preferable that the catalyst contains at least one kind of metal selected from the group consisting of aluminum, chromium, manganese, zirconium, titanium and magnesium as a main component and at least one kind of metal selected from the group consisting of aluminum, chromium, titanium, manganese, iron, nickel, copper, cobalt, magnesium, zirconium, molybdenum, niobium, tantalum and antimony as a sub component (provided that the main component and the sub component are different metals).

The following forms are conceivable for the catalyst in which two or more kinds of metals are contained in combination:

(a) a metal material formed from a plurality of metal species is filled into a reactor and as a whole used as a "solid catalyst";

(b) a metal material containing a first metal is impregnated with a solution (such as aqueous solution) containing a second metal (and optionally third or more metals) so that the second metal (and optionally third or more metals) is supported on the first metal-containing material, and then, is filled into a reactor; and (c) a "metal-free solid catalyst" such as activated catalyst is used as a support and impregnated with a solution containing a plurality of metals.

Any of these catalyst forms can be applied.

In the following, an explanation will be given of the catalyst forms (a) and (b).

The catalyst form (a) is implemented by alloying the metal and subjecting the resulting alloyed metal to oxidation treatment and optionally fluorination treatment. Even without such an alloying process, a mixture of alumina and chromia, alumina and zirconia, alumina and titania, or alumina and magnesia (or a fluorination product of the mixture) can be applied as the catalyst (a).

On the other hand, the catalyst form (b) is an easy technique to utilize an oxide or fluoride of the first metal as a main component and add a second metal (and optionally third and fourth metals) as a sub component. The catalyst of this form is also called "supported catalyst" in the meaning that that the "second metal (and optionally third and fourth metals) is supported on the "first metal". As exemplified in the after-mentioned working examples, a "chromium-supported alumina catalyst" and a "chromium-supported partially fluorinated alumina catalyst" can be particularly suitably applied as the catalyst (b) because each of these catalysts is especially stable and capable of smoothly converting the halogenated $C_3$ hydrocarbon compound represented by the general formula (1) to the target trans-1-chloro-3,3,3-trifluoropropene compound.

In the case of using a plurality of metals in the solid catalyst, it is preferable to contain aluminum as a main metal component in each of the catalyst forms (a) and (b). More specifically, the catalyst preferably contains aluminum in an amount of 50 atomic % or more based on the total amount of the metal components in order to let the fluorination reaction proceed with a good conversion rate. The catalyst particularly preferably contains aluminum in an amount of 80 atomic % or more. Although the catalyst may contain a single metal component (e.g. aluminum), it is feasible to impart a further improved catalytic activity to the catalyst by the addition of 0.1 to 20 atomic % of a sub metal component (see the after-mentioned working examples). It is an especially preferable example to use 90 to 99 atomic % of aluminum and 1 to 10 atomic % of chromium in combination.

In some cases, the "metal oxide" usable as the solid catalyst or the raw material for the "partially fluorinated metal oxide" or "metal fluoride" in the present invention exists in more than one crystalline form. For example, alumina includes γ-alumina and α-alumina; and titania are in anatase and rutile crystalline forms. The metal oxide can be of any crystalline form. In the case of using alumina, γ-alumina is preferred because of its large surface area.

As mentioned above, the "partially fluorinated metal oxide (fluorinated metal oxide)" is preferred as the solid catalyst in the present invention. There are no particular limitations on the method for preparing the "partially fluorinated metal oxide (fluorinated metal oxide)" and the method for preparing the "metal fluoride" by further fluorination of the "partially fluorinated metal oxide (fluorinated metal oxide)". For example, the fluorinated metal oxide or metal fluoride can be obtained by bringing the above-mentioned "metal oxide (including multiple metal oxide)" into contact with a fluorination agent such as hydrogen fluoride, fluorinated hydrocarbon or fluorinated chlorinated hydrocarbon. In general, it is preferable to perform this fluorination treatment in a stepwise manner. In view of the fact that the fluorination treatment of a solid catalyst such as metal oxide with hydrogen fluoride is accompanied with large heat generation, it is preferable to first perform the fluorination treatment with a diluted aqueous hydrofluoric acid solution or hydrogen fluoride gas at a relatively low temperature and then perform the fluorination treatment by increasing the hydrofluoric acid or hydrogen fluoride concentration and/or fluorination treatment temperature. The final stage of the fluorination treatment is preferably performed at a temperature higher than or equal to the temperature of the "fluorination reaction of the halogenated $C_3$ hydrocarbon compound represented by the general formula (1)". In addition to this condition, it is preferable to perform the fluorination treatment with hydrogen fluoride at a temperature of 100° C. or higher, more preferably 200° C. or higher, still more preferably 300° C. or higher, in order to let the reaction proceed more stably. There is no upper limit of the fluorination treatment temperature. It is however difficult to perform the fluorination treatment at a temperature exceeding 900° C. from the viewpoint of the durability of the fluorination treatment equipment. Thus, the fluorination treatment temperature is practically preferably 600° C. or lower.

Furthermore, it is preferable to perform fluorination treatment on the metal oxide or metal fluoride catalyst with a fluorination agent such as HF immediately before use in the present invention. The fluorination treatment can be performed in accordance with the above-mentioned preparation method of the metal fluoride or partially fluorinated metal oxide. It is particularly preferable to, even in the case where the metal fluoride or partially fluorinated metal oxide catalyst is prepared by the above-mentioned method, newly perform fluorination treatment on the catalyst at a predetermined temperature before use in order to let the desired fluorination reaction of the halogenated $C_3$ hydrocarbon compound proceed stably. From the viewpoint of easy operation and high effect, this fluorination treatment is preferably performed in the same reactor as the fluorination reaction of the present invention during a time period after filling the solid catalyst into the reactor and before starting the desired reaction.

[Supported Catalyst]

In the present invention, a supported catalyst in which a metal compound is supported on a support (corresponding to the above-mentioned catalyst forms (b) and (c)) is particularly preferred as the solid catalyst. The "supported catalyst" will be explained in detail below although some of the following explanation overlap the foregoing explanation.

As a support of the supported catalyst, there can be used carbon (such as activated carbon) or any of the above-mentioned metal compounds (including multiple metal oxide). In the case of using the metal compound as the support, the above-mentioned metal oxide or fluorination product thereof such as "metal fluoride" or "partially fluorinated metal oxide" can suitably be used. Preferable examples of the metal compound usable as the support are oxide, fluoride or partially fluorinated oxide of at least one kind of metal selected from the group consisting of aluminum, chromium, manganese, zirconium, titanium and magnesium.

A multiple metal oxide can also be used as the support. Preferable examples of the multiple metal oxide as the support are metal oxides containing at least one kind of metal selected from the group consisting of aluminum, chromium, manganese, zirconium, titanium and magnesium as a main metal component and at least one kind of metal selected from the group consisting of aluminum, chromium, titanium, manganese, iron, nickel, copper, cobalt, magnesium, zirconium, molybdenum, niobium, tantalum and antimony as a sub metal component.

By definition, the "supported catalyst" is a catalyst obtained by impregnating the support with a "solution of metal". Thus, the "supported catalyst" allows combined use of multiple metals in the case of using a metal oxide as the "support" and a different metal oxide as the "metal compound to be supported (also referred to as "supported material" in the present specification)". In such a case, the necessity for intentionally using multiple metals in the support is not always high. However, the present invention does not exclude the case where the multiple metal oxide support is selected as desired by a person skilled in the art.

As a metal contained in the "metal compound to be supported (supported material)", there can suitably be used aluminum, chromium, titanium, manganese, iron, nickel, cobalt, copper, magnesium, zirconium, molybdenum, zinc, tin, lanthanum, niobium, tantalum and antimony. Among others, aluminum, chromium, titanium, iron, nickel, cobalt, copper, zirconium, zinc, tin, lanthanum, iobium, tantalum and antimony are preferred. These metals are each supported in the form of a fluoride, chloride, fluorochloride, oxyfluoride, oxychloride or oxyfluorochloride. It is feasible to support one kind of metal compound solely or two or more kinds of metal compounds in combination. Since the "supported catalyst" is formed as a metal composite catalyst by impregnating the support with a solution of the supported metal, different compounds are principally used as the "the metal compound to be supported (supported material)" and the "support".

Specific examples of the supported material include, but are not limited to, chromium nitrate, chromium trichloride, potassium dichromate, titanium tetrachloride, manganese nitrate, manganese chloride, ferric chloride, nickel nitrate, nickel chloride, cobalt nitrate, cobalt chloride, antimony pentachloride, magnesium chloride, magnesium nitrate, zirconium chloride, zirconium oxychloride, zirconium nitrate, copper (II) chloride, zinc (II) chloride, lanthanum nitrate and tin tetrachloride. It is preferable to support the supported material on the support by bringing a solution (normally, aqueous solution) of the supported metal into contact with the support, impregnating the support with the metal compound and then evaporating water under heating (see the after-mentioned preparation example 3). In the case where the metal chloride liquid at ordinary temperatures, such as titanium tetrachloride, antimony pentachloride or tin tetrachloride is used, it is preferable to support a neat liquid of the metal chloride, rather than a solution of the metal chloride, on the support.

For stable progress of the reaction, the catalyst in which the above metal compound is supported on the support may be and is preferably subjected to fluorination treatment before use. Namely, it is preferable to perform fluorination treatment on the supported catalyst with a fluorination agent such as hydrogen fluoride, fluorinated hydrocarbon or fluorinated chlorinated hydrocarbon at a temperature higher than or equal to a predetermined reaction temperature before use as in the case of the other solid catalyst.

Preferable examples of the fluorination catalyst usable in the present invention are chromium-supported fluorinated alumina, fluorinated alumina and chromium-supported activated carbon. Among others, chromium-supported fluorinated alumina and fluorinated alumina are particularly preferred. It is preferable to perform fluorination treatment on the fluorination catalyst with a fluorination agent such as HF before use in the reaction.

The mass ratio of the metal is generally 0.1 to 80 mass %, preferably 1 to 50 mass %, based on the total mass of the catalyst including the support and the supported material. When the mass ratio of the metal is 0.1 mass % or more, the catalyst shows a good catalytic activity. When the mass ratio of the metal is 80 mass % or less, the metal can be stably supported. In the case where the supported material is a solid metal salt, the mass ratio of the metal is generally 0.1 to 40 mass %, preferably 1 to 30 mass %, based on the total mass of the catalyst.

[Production Process of Trans-1-chloro-3,3,3-trifluoropropene]

The molar ratio of the halogenated $C_3$ hydrocarbon compound and hydrogen fluoride fed to the reaction system is varied depending on the temperature of the reaction and is generally in a range of 1/1 to 1/20, preferably 1/1 to 1/10. When the hydrogen fluoride is used in an amount of more than 20 molar times the halogenated $C_3$ hydrocarbon compound, there may occur a decrease of organic substance processing amount in the same reactor and a trouble in separating a mixture of unreacted hydrogen fluoride and the reaction product discharged from the reaction system. When the hydrogen fluoride is used in an amount of less than 1 molar time the halogenated $C_3$ hydrocarbon compound, there unfavorably occurs a decrease of selectivity with a decrease of reaction rate.

The molar ratio of the halogenated $C_3$ hydrocarbon compound and chorine fed into the reaction system is also varied depending on the temperature of the reaction and is generally in a range of 1/0.001 to 1/0.5, preferably 1/0.01 to 1/0.1, more preferably 1/0.01 to 1/0.05. When the chlorine is used in an amount of more than 0.5 molar times the halogenated $C_3$ hydrocarbon compound, there is unfavorably generated an increased amount of a perchloride. When the chlorine is used in an amount of less than 0.001 molar times the halogenated $C_3$ hydrocarbon compound, there unfavorably occurs a decrease of conversion rate with a decrease of reaction rate.

Unreacted hydrogen fluoride can be separated from unreacted organic substance and the reaction product and recycled in the reaction system. It is feasible to separate the hydrogen fluoride and the organic substances by any known technique.

There is no particular limitation on the temperature of the reaction in the present invention. The reaction temperature is generally 100° C. to 500° C., preferably 150° C. to 400° C., more preferably 150° C. to 300° C. When the reaction temperature is lower than 100° C., the reaction is slow and impractical. When the reaction temperature is higher than 500° C., there is unfavorably generated an increased amount of tar product or decomposition product. In the present invention, the use of the solid catalyst makes it possible to achieve, even at a lower temperature (more specifically, a temperature lower than 300° C.), a high 1233E yield comparable to that achieved at a "temperature higher than 300° C." as compared to the case of using the solid catalyst as mentioned above. Consequently, the present invention provides large merits such as less load on the reactor and less amount of energy consumption During the reaction, the halogenated $C_3$ hydrocarbon compound may be fed, together with a non-reacting diluent gas such as nitrogen, helium or argon, to the reaction system. The ratio of such a diluent gas used per 1 mol of the halogenated $C_3$ hydrocarbon compound is generally 100 mol or less, preferably 10 mol or less. As the reaction of the present invention is carried out in a gas phase, the feeding of the non-reacting diluent gas results in a decrease of productivity due to dilution of the raw material. Further, it has been found that there is less adverse effect on the selectivity even when the reaction is performed in the absence of the diluent gas. For these reasons, it is generally preferable to not use the diluent gas.

There is no particular limitation on the pressure during the reaction in the present invention. The reaction can be performed under atmospheric pressure without pressure control such as pressurization or pressure reduction. From the viewpoint of the equipment, the reaction pressure is preferably 0.01 to 1 MPa (in terms of absolute pressure in the present specification; the same applies to the following). The reaction needs to be performed with caution under pressurized conditions due to the fact that, under pressurized conditions, the equilibrium of the reaction system may shift in a direction that causes undesired addition reaction. On the other hand, the reaction can be performed under reduced pressure conditions. It is desirable to determine the pressure conditions such that the organic substances such as raw material present in the reaction system do not liquefy in the reaction system.

The contact time of the reaction (i.e. reaction time) in the present invention is generally 1 to 500 seconds, preferably 10 to 300 seconds, under standard conditions (0° C. and 1 atmospheric pressure). When the contact time is short, there unfavorably occurs a decrease of reaction rate. When the contact time is too long, there unfavorably occurs a side reaction.

The reaction of the present invention is performed by substantially simultaneously introducing the halogenated $C_3$ hydrocarbon compound, hydrogen fluoride and chloride into the reactor while controlling the temperature. In general, the reactor is tubular in shape and is made of or lined with stainless steel, Hastelloy™, Monel™, platinum, carbon or fluorocarbon resin.

In the present invention, the halogenated $C_3$ hydrocarbon compound is preferably at least one selected from the group consisting of 1,1,3,3-tetrachloro-1-fluoropropane (241fa), 1,1,1,3,3-pentachloropropane (240fa) and 1,3,3-trichloro-1, 1-difluoropropane (242fa). When this halogenated $C_3$ hydrocarbon compound is used as the raw organic substance, trans-1-chloro-3,3,3-trifluoropropene is efficiently produced by gas-phase reaction of the raw organic substance with hydrogen fluoride in the presence of the solid catalyst and chlorine.

[Production of Trans-1-chloro-3,3,3-trifluoropropene using 1,1,1,3,3-Pentachloropropane as Starting Material]

A production method of trans-1-chloro-3,3,3-trifluoropropene using 1,1,1,3,3-pentachloropropane (240fa) as a raw organic substance will be now explained below. In one embodiment of the present invention, the production method includes a step (A) of reacting 1,1,1,3,3-pentachloropropane (240fa) with hydrogen fluoride and a step (B) of forming trans-1-chloro-3,3,3-trifluoropropene by reacting the intermediate product obtained in the step (A) with hydrogen fluoride in a gas phase in the presence of the solid catalyst and chlorine.

Figure 1:
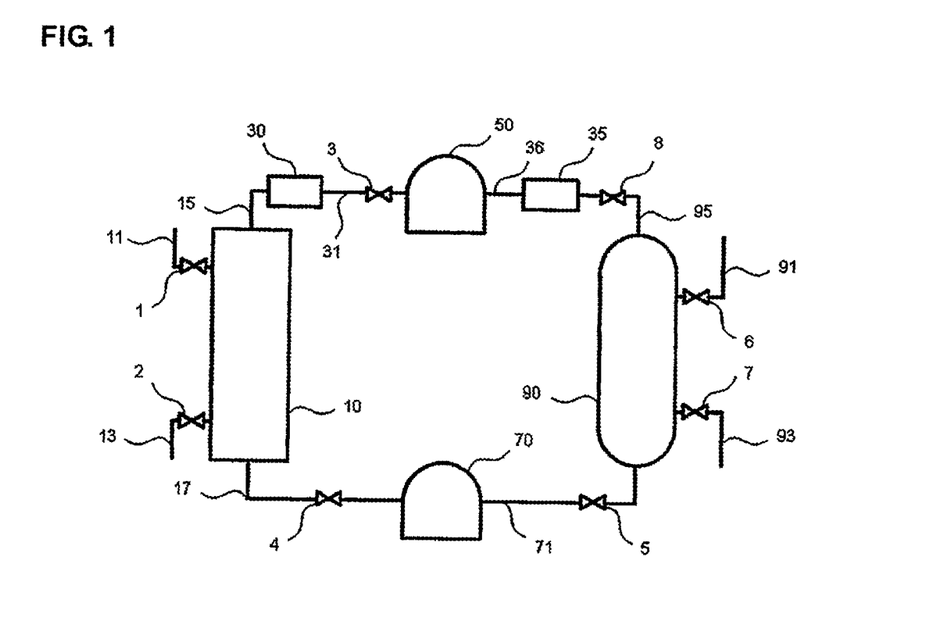
FIG. 1 is a schematic view of a production device 100 according to one embodiment of the present invention.

FIG. 1 is a schematic view of a production device 100 according to one embodiment of the present invention. The production device 100 has, for example, a liquid-phase reaction chamber 10, a condenser 30, a tank 50, a tank 70 and a gas-phase reaction column 90. However, the production device 100 is not limited to such a structure.

The liquid-phase reaction chamber 10 is in the form of e.g. a stainless steel autoclave. The raw organic substance is fed to the liquid-phase reaction chamber 10 from a pipe 11 via a valve 1. Hydrogen fluoride is also fed to the liquid-phase reaction chamber 10 from a pipe 13 via a valve 2. Although the starting organic substance and hydrogen fluoride are fed from different pipes in the embodiment of FIG. 1, it is alternatively feasible to feed the starting organic substance and hydrogen fluoride individually or as a mixture thereof from a single pipe to the liquid-phase reaction chamber 10.

A pipe 15 is connected at one end side thereof to the top of the liquid-phase reaction chamber 10 and at the other end side thereof to the condenser 30. A pipe 31 is connected at one end side thereof to the condenser 30 and at the other end side thereof to the tank 50 via a valve 3. The tank 50 is configured to store trans-1-chloro-3,3,3-trifluoropropene liquefied in the condenser 30. A pipe 17 is connected at one end side thereof to the bottom of the liquid-phase reaction chamber 10 and at the other end side thereof to the tank 70 via a valve 4. The reaction liquid of the liquid-phase reaction chamber 10, which contains the intermediate product, is stored in the tank 70.

A pipe 71 is connected at one end side thereof to the tank 70 and at the other end side thereof to the gas-phase reaction column 90 via a valve 5. A pipe 91 is also connected to the gas-phase reaction column 90 via a valve 6 so as to feed chlorine into the gas-phase reaction column 90. Further, a pipe 93 is connected to the gas-phase reaction column 90 via a valve 7 so as to feed hydrogen fluoride into the gas-phase reaction column 90. The gas-phase reaction column 90 is filled with the solid catalyst. Although chlorine and hydrogen fluoride are fed from different pipes in the embodiment of FIG. 1, it is alternatively feasible to feed chlorine and hydrogen fluoride individually or as a mixture from a single pipe to the gas-phase reaction column 90.

A pipe 95 is connected at one end side thereof to the top of the gas-phase reaction column 90 and at the other end side thereof to a condenser 35 via a valve 8. The condenser 35 is connected to the tank 50 via a pipe 36. The tank 50 is configured to store trans-1-chloro-3,3,3-trifluoropropene liquefied in the condenser 35. Although the trans-1-chloro-3,3,3-trifluoropropene products of two systems are stored in a common tank 50 in the embodiment of FIG. 1, it is alternatively feasible to store the products of these two systems in different tanks.

In one embodiment, the production method can be implemented as follows. In the step (A), 1,1,1,3,3-pentachloropropane (240fa) is reacted with hydrogen fluoride in the liquid-phase reaction chamber 10. In the step (B), the intermediate product obtained in the step (A) is introduced into the gas-phase reaction column 90 and reacted in a gas phase with hydrogen fluoride in the presence of the solid catalyst and chlorine to form trans-1-chloro-3,3,3-trifluoropropene. The reaction product gas of the liquid-phase reaction chamber 10, which contains trans-1-chloro-3,3,3-trifluoropropene, is extracted from the liquid-phase reaction chamber 10 via the pipe 15, liquefied in the condenser 30 and then recovered into the tank 50. Herein, 1,1,1,3,3-pentachloropropane (240fa) and hydrogen fluoride can be introduced continuously or introduced intermittently by opening and closing the valve 3; and trans-1-chloro-3,3,3-trifluoropropene can be recovered continuously or recovered intermittently by opening and closing the valve 3.

On the other hand, the reaction liquid of the liquid phase reaction chamber 10, which contains the intermediate product, is recovered into the tank 70 via the pipe 17. The reaction liquid recovered and stored in the tank 70 is fed to the gas-phase reaction column 90 via the pipe 71. In the gas-phase reaction column 90, the intermediate product (the above-mentioned halogenated $C_3$ hydrocarbon compound) contained in the reaction liquid is reacted with hydrogen fluoride in a gas phase in the presence of the solid catalyst and chlorine. There is thus produced trans-1-chloro-3,3,3-trifluoropropene. Herein, the above-mentioned $C_3$ hydrocarbon compound may be added to the reaction liquid stored in the tank 70 and reacted as the raw reaction material with hydrogen fluoride in the gas-phase reaction column 90. The reaction product gas of the gas-phase reaction column 90, which contains trans-1-chloro-3,3,3-trifluoropropene, is extracted from the gas-phase reaction column 90 via the pipe 95, and liquefied in the condenser 35 and recovered into the tank 50 via the pipe 36.

The method for reacting 1,1,1,3,3-pentachloropropane with hydrogen fluoride is not limited to the above-mentioned embodiment. Any known method can be adopted for reaction of 1,1,1,3,3-pentachloropropane with hydrogen fluoride. For example, it is feasible to adopt a gas-phase reaction method (see Japanese Laid-Open Patent Publication No. H09-18374) or a liquid-phase reaction method (see Japanese Laid-Open Patent Publication No. H11-180908). The reaction method is however not limited to these examples.

The method for reacting 1,1,1,3,3-pentachloropropane with hydrogen fluoride is not limited to the above-mentioned embodiment. Any known method can be adopted for reaction of 1,1,1,3,3-pentachloropropane with hydrogen fluoride. For example, it is feasible to adopt a gas-phase reaction method (see Japanese Laid-Open Patent Publication No. H09-183740) or a liquid-phase reaction method (see Japanese Laid-Open Patent Publication No. H11-180908). The reaction method is however not limited to these examples.

The intermediate product obtained by reacting 1,1,1,3,3-pentachloropropane with hydrogen fluoride is reacted with hydrogen fluoride in a gas phase in the presence of chlorine. By this reaction, trans-1-chloro-3,3,3-trifluoropropane is produced. The method for reacting the intermediate product with hydrogen fluoride in a gas phase in the presence of the solid catalyst and chlorine can be described in accordance with the method for reacting the halogenated $C_3$ hydrocarbon compound with hydrogen fluoride in a gas phase in the presence of the solid catalyst chlorine as described above, namely, by replacing the "halogenated $C_3$ hydrocarbon compound" with the "intermediate product".

Not only trans-1-chloro-3,3,3-trifluoropropene as the target compound, but also an unreacted fraction of the intermediate product and any reaction by-product may be contained in the reaction mixture obtained by the reaction of the step (B). It is feasible to extract and feed these unreacted and by-product components to the reaction system of the step (B) for efficient production of the target trans-1-chloro-3,3,3-trifluoropropene compound.

There is no particular limitation on the method for separating trans-1-chloro-3,3,3-trifluoropropene from the reaction mixture. The separation may be conducted by e.g. distillation. To facilitate the separation, it is feasible to subject the reaction mixture to e.g. washing with other as required and thereby remove an acidic component possibly contained in the reaction mixture.

Although the target compound, trans-1-chloro-3,3,3-trifluoropropene, is formed in the reaction of the step (B), cis-1-chloro-3,3,3-trifluoropropene may also be formed simultaneously. In this case, it is feasible to extract cis-1-chloro-3,3,3-trifluoropropene from the reaction mixture and feed the extracted cis-1-chloro-3,3,3-trifluoropropene to the reaction system of the step (B) as described above or feasible to separately isomerize cis-1-chloro-3,3,3-trifluoropropene to trans-1-chloro-3,3,3-trifluoropropene by heating at 150° C. to 600° C.

When the gas-phase fluorination of a halogenated hydrocarbon compound high in boiling point, in particular high in chlorination degree, is ordinarily performed in the presence of a solid catalyst, the yield of trans-1-chloro-3,3,3-trifluoropropene may be decreased with decrease in the activity of the catalyst due to the generation of a tar product etc. (see the after-mentioned comparative example 1). It is however possible in the present invention to significantly suppress a decrease of catalyst activity by performing this fluorination reaction in the presence of chlorine. Accordingly, the method of the present invention established as an industrial production method.

In this way, the present invention enables efficient production of trans-1-chloro-3,3,3-trifluoropropene from 1,1,1,3,3-pentachloropropane (240fa) as the raw material by efficient consumption of the low-reactivity intermediate product.

EXAMPLES

The production method of trans-1-chloro-3,3,3-trifluoropropene according to the present invention will be described in more detail below by way of the following examples. It should however be noted that the following examples are illustrative and are not intended to limit the present invention thereto.

Preparation Example 1

Into a 2000-ml stainless steel autoclave equipped with a condenser through which a cooling fluid of 100° C. was circulated, 1,1,1,3,3-pentachloropropane (240fa) and hydrogen fluorine were respectively introduced at 4.1 g/min and 3.4 g/min (i.e. at a molar ratio of 240 fa/hydrogen fluoride=1/10). Then, the autoclave was heated at 150° C. At the time when the pressure inside the autoclave exceeded about 4 MPa, the reaction product gas containing 1233E as a main component was extracted from a needle valve at the exit of the condenser such that the pressure was maintained at about 4 MPa. The extracted reaction product gas was passed through a fluororesin-made gas washing bottle filled with ice water and cooled in an ice bath, so that acid components in the reaction product gas were removed by absorption. After that, the reaction product gas was recovered as product organic substances in a glass trap cooled in a dry ice-acetone bath.

At the time when the quantity of the reaction fluid in the autoclave reached 1000 ml, the reaction fluid was drained from a dip tube of the autoclave via a needle valve such that the liquid quantity was maintained at 1000 ml. The drained reaction liquid was recovered into a fluororesin-made gas washing bottle filled with ice water and cooled in an ice bath. After the reaction was continued for 24 hours, all the reaction liquid in the autoclave was recovered into the fluororesin-made gas washing bottle filled with ice water. The amount of the product organic substances recovered from the outlet of the condenser was 2952 g in total. The amount of the reaction liquid drained from the dip tube was 1879 g in total. The same reaction operation was repeated nine times. The total amount of the recovered reaction liquid was 19.1 kg. The recovered reaction liquid was distilled in a glass distillation column, thereby obtaining 10.9 kg of a fraction at 100° C. to 145° C. The reaction liquid and the fraction were analyzed by gas chromatography. The analysis results are shown in TABLE 1.

In TABLE 1, 1233E refers to trans-1-chloro-3,3,3-trifluoropropene (1233zd(E)); and 1233Z refers to cis-1-chloro-3,3,3-trifluoropropene (1233zd(Z)).

The "fraction" obtained in Preparation Example 1 was used as a raw material (i.e. a liquid composition containing a halogenated $C_3$ hydrocarbon) in Examples 1 to 6 and Comparative Example 1 as explained below.

TABLE 1

| | GC area % | | | | | | |
|---|---|---|---|---|---|---|---|
| | 1233E | 244fa | 1233Z | 243fa | 242fa | 241fa | 240fa |
| Reaction liquid | 0.25 | 1.53 | 2.12 | 4.11 | 32.83 | 41.36 | 0.98 |
| Fraction | nd | nd | nd | 3.93 | 54.80 | 25.84 | nd |

Note:
A plurality of intermediate compounds other than those listed in the table were contained in trace amounts in each of the reaction liquid and the fraction.
The term "nd" means less than 0.01 GG area %.

Preparation Example 2

Preparation of Fluorinated Alumina Catalyst

A reaction tube, which was made of stainless steel (SUS316L) in a cylindrical shape with a diameter of 2.7 cm and a length of 40 cm and equipped with an electric furnace, was filled with 130 ml of γ-alumina (available as "KHS-4" from Sumika Alchem Co., Ltd.). The reaction tube was heated to 200° C. while feeding nitrogen gas through the reaction tube. When the effusion of water was no longer seen, hydrogen fluoride (HF) was fed together with nitrogen gas into the reaction tube. The concentration of hydrogen fluoride fed was gradually increased. The filled alumina was subjected to fluorination treatment by, when a hot spot due to fluorination of the filled alumina reached an outlet end of the reaction tube, raising the temperature of the reaction tube in steps of 100° C. and maintaining the reaction tube for 1 hour at each temperature. In the fluorination treatment, the reaction tube was finally heated up to 400° C. and maintained for 1 hour under such a heating state. There was thus obtained a fluorinated alumina catalyst.

Preparation Example 3

Preparation of Chromium-Supported Fluorinated Alumina Catalyst

An aqueous solution of 20 mass % chromium chloride was prepared in a conical flask. Then, 130 ml of the fluorinated alumina prepared in Preparation Example 2 was immersed and maintained in the aqueous chromium chloride solution for 3 hours. The immersed fluorinated alumina was filtered out and dried at 70° C. under a reduced pressure by means of a rotary evaporator. There was thus obtained a chromium-supported fluorinated alumina catalyst.

A reaction tube, which was made of stainless steel (SUS316L) in a cylindrical shape with a diameter of 2.7 cm and a length of 40 cm and equipped with an electric furnace, was filled with the above chromium-supported fluorinated alumina catalyst. The reaction tube was heated to 200° C. while feeding nitrogen gas through the reaction tube. When the effusion of water was no longer seen, hydrogen fluoride (HF) was fed together with nitrogen gas into the reaction tube. The concentration of hydrogen fluoride fed was gradually increased. The filled catalyst was subjected to fluorination treatment by, when a hot spot due to fluorination of the filled catalyst reached an outlet end of the reaction tube, raising the temperature of the reaction tube in steps of 100° C. and maintaining the reaction tube for 1 hour at each temperature. In the fluorination treatment, the reaction tube was finally maintained at 400° C. for 1 hour. By such fluorination treatment, the chromium-supported fluorinated alumina catalyst was activated.

Example 1

A reaction tube, which was made of stainless steel (SUS316L) in a cylindrical shape with an inner diameter of 2.7 cm and a length of 40 cm and equipped with an electric furnace, was filled with 130 ml of the chromium-supported fluorinated alumina catalyst prepared in Preparation Example 3. The temperature of the reaction tube was raised while feeding nitrogen at 10 ml/min into the reaction tube. At the time when the temperature of the reaction tube reached 150° C., a gasified product of the fraction obtained in Preparation Example 1 (that is, the liquid composition containing the halogenated $C_3$ hydrocarbon), hydrogen fluoride and chlorine were respectively fed as the raw reaction materials at 0.30 g/min, 0.10 g/min and 1.0 ml/min (molar ratio: halogenated $C_3$ hydrocarbon/hydrogen fluoride/chlorine=1/3.28/0.028, contact time: 51 seconds). The feeding of nitrogen was stopped when the flow rates of the raw reaction materials were stabilized.

Herein, the mole number of the "halogenated $C_3$ hydrocarbon" was determined as the sum of the molar amounts of respective halogenated $C_3$ hydrocarbon compounds calculated from GC % of the gas chromatography analysis result.

A product gas from the reaction tube was passed through a fluororesin-made gas washing bottle filled with ice water and cooled in an ice bath, so as to absorb unreacted hydrogen fluoride and hydrogen chloride and trap the reaction product. The reaction product was analyzed by gas chromatography. The analysis results are shown in TABLE 3. In TABLE 3, 1234E refers to trans-1,3,3,3-tetrafluoropropene (1234ze (E)); 1234Z refers to cis-1,3,3,3-tetrafluoropropene (1234ze (Z)); 1233E refers to trans-1-chloro-3,3,3-trifluoropropene (1233zd(E)); and 1233Z refers to cis-1-chloro-3,3,3-trifluoropropene (1233zd(Z)).

Example 2

The reaction was conducted in the same manner as in Example 1, except that, when the temperature of the reaction tube reached 200° C., a gasified product of the fraction obtained in Preparation Example 1 (that is, the liquid composition containing the halogenated $C_3$ hydrocarbon), hydrogen fluoride and chlorine were respectively fed as the raw reaction materials at 0.39 g/min, 0.09 g/min and 1.0 ml/min (molar ratio: halogenated $C_3$ hydrocarbon/hydrogen fluoride/chlorine=1/2.23/0.022, contact time: 52 seconds). The results are shown in TABLE 3.

Example 3

The reaction was conducted in the same manner as in Example 1, except that, when the temperature of the reaction tube reached 250° C., a gasified product of the fraction obtained in Preparation Example 1 (containing the halogenated $C_3$ hydrocarbon), hydrogen fluoride and chlorine were respectively fed as the raw reaction materials at 0.25 g/min, 0.06 g/min and 1.0 ml/min (molar ratio: halogenated $C_3$ hydrocarbon/hydrogen fluoride/chlorine=1/2.26/0.033, contact time: 80 seconds). The results are shown in TABLE 3.

Example 4

The reaction was conducted in the same manner as in Example 1, except that, when the temperature of the reaction tube reached 300° C., a gasified product of the fraction obtained in Preparation Example 1 (containing the halogenated $C_3$ hydrocarbon), hydrogen fluoride and chlorine were respectively fed as the raw reaction materials at 0.26 g/min, 0.07 g/min and 1.0 ml/min (molar ratio: halogenated $C_3$ hydrocarbon/hydrogen fluoride/chlorine=1/2.37/0.032, contact time: 74 seconds). The results are shown in TABLE 3.

The reaction temperatures, contact times and raw reaction material feeding amounts of Examples 1 to 4 are summarized in TABLE 2.

TABLE 2

| | Reaction temp. ° C. | Contact time (s) | Average flow rate (Molar ratio) | | |
| --- | --- | --- | --- | --- | --- |
| | | | Organic substances | Hydrogen fluoride | Chlorine |
| Example 1 | 150 | 51 | 1 | 3.3 | 0.028 |
| Example 2 | 200 | 52 | 1 | 2.23 | 0.022 |
| Example 3 | 250 | 80 | 1 | 2.3 | 0.033 |
| Example 4 | 300 | 74 | 1 | 2.4 | 0.032 |

Note:
The term "organic substances" in TABLE 2 refers to 243fa, 242fa and 241fa as "halogenated $C_3$ hydrocarbon". The mole number of the halogenated $C_3$ hydrocarbon was determined as the sum of the mole numbers of these organic substance compounds calculated from GG area %.

TABLE 3

| | GC area % | | | | | | | |
|---|---|---|---|---|---|---|---|---|
| | 245fa | 1233E | 244fa | 1233Z | 1223Z | 243fa | 242fa | 241fa |
| Example 1 | 3.07 | 45.79 | 8.47 | 3.87 | 1.84 | 22.45 | 8.71 | nd |
| Example 2 | 5.54 | 73.58 | 1.06 | 6.39 | 3.13 | 2.32 | nd | nd |
| Example 3 | 2.13 | 76.94 | 0.51 | 7.18 | 5.86 | 0.89 | 0.01 | nd |
| Example 4 | 0.72 | 77.11 | 0.20 | 8.61 | 6.74 | 0.31 | 0.01 | nd |

The term "nd" means less than 0.01 GG area %.

As shown above, the formation of 1233E as the target compound was confirmed in Examples 1 to 4. In particular, the GC area % yield of 1223E was high in Examples 2 to 4 where the reaction temperature was 200° C. or higher.

Comparative Example 1

The reaction was conducted for 1 hour in the same manner as in Example 1, except that the feeding amounts of the raw reaction materials were changed by feeding a gasified product of the fraction obtained in Preparation Example 1 (that is, the liquid composition containing the halogenated $C_3$ hydrocarbon), hydrogen fluoride and chlorine respectively at 0.41 g/min, 0.11 g/min and about 1.0 ml/min (molar ratio: halogenated $C_3$ hydrocarbon/hydrogen fluoride/chlorine=1/2.36/0.020, contact time: 47 seconds). After that, the reaction was then continued in a state where the feeding of chlorine was stopped. The analysis of the reaction product was again performed after a lapse of 8 hours and after a lapse of 13 hours. The results are shown in TABLE 4.

TABLE 4

| Comparative Example 1 | GC area % | | | | | | | |
|---|---|---|---|---|---|---|---|---|
| | 245fa | 1233E | 244fa | 1233Z | 1223Z | 243fa | 242fa | 241fa |
| 1 h (with chlorine) | 6.38 | 74.35 | 1.11 | 6.31 | 2.69 | 2.09 | nd | nd |
| 8 h | 5.31 | 69.67 | 1.41 | 6.32 | 1.80 | 3.75 | nd | nd |
| 13 h | 5.30 | 61.78 | 4.96 | 6.56 | 2.04 | 9.74 | 4.10 | nd |

The term "nd" means less than 0.01 GG area %.

It has been shown by the results of Comparative Example 1 that, when chlorine is not fed as the raw reaction material, the rate of conversion of the raw organic material and the yield of 1233 gradually decreases with time.

Example 5

Figure 2:
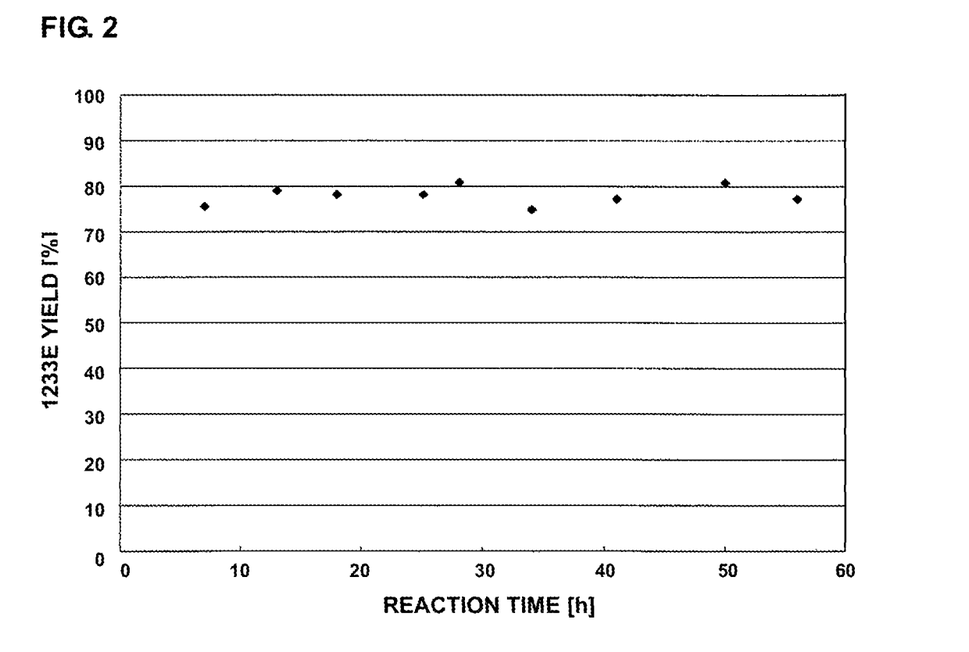

A reaction tube, which was made of stainless steel (SUS316L) in a cylindrical shape with an inner diameter of 2.7 cm and a length of 40 cm and equipped with an electric furnace, was filled with 130 ml of the chromium-supported fluorinated alumina catalyst prepared in Preparation Example 3. The temperature of the reaction tube was raised while feeding nitrogen at 10 ml/min into the reaction tube. At the time when the temperature of the reaction tube reached 250° C., a gasified product of the fraction obtained in Preparation Example 1 (that is, the liquid composition containing the halogenated $C_3$ hydrocarbon), hydrogen fluoride and chlorine were respectively fed as the raw reaction materials at 0.51 g/min, 0.08 g/min and 1.0 ml/min (molar ratio: halogenated $C_3$ hydrocarbon/hydrogen fluoride/chlorine=1/1.54/0.017, contact time: 50 seconds). The feeding of nitrogen was stopped when the flow rates of the raw reaction materials were stabilized. A product gas from the reaction tube was passed through a fluororesin-made gas washing bottle filled with ice water and cooled in an ice bath, so as to absorb unreacted hydrogen fluoride and hydrogen chloride and trap the reaction product. The reaction product was analyzed by gas chromatography. The analysis results of changes in reaction yield over time are shown in FIG. 2. In FIG. 2, the term "122E yield" means the concentration (GC %) of 1233E in the reaction product.

As is seen from FIG. 2, the catalytic activity of the chromium-supported fluorinated alumina catalyst was maintained at a favorable level over 60 hours in the present invention.

Example 6

A reaction tube, which was made of stainless steel (SUS316L) in a cylindrical shape with an inner diameter of 2.7 cm and a length of 40 cm and equipped with an electric furnace, was filled with 130 ml of the fluorinated alumina catalyst prepared in Preparation Example 2. The temperature of the reaction tube was raised while feeding nitrogen at 10 ml/min into the reaction tube. At the time when the temperature of the reaction tube reached 280° C., a gasified product of the fraction obtained in Preparation Example 1 (containing the halogenated $C_3$ hydrocarbon), hydrogen fluoride and chlorine were respectively fed as the raw reaction materials at 0.64 g/min, 0.12 g/min and 1.0 ml/min (molar ratio: halogenated $C_3$ hydrocarbon/hydrogen fluoride/chlorine=1/1.75/0.013, contact time: 37 seconds). The feeding of nitrogen was stopped when the flow rates of the raw reaction materials were stabilized. A product gas from the reaction tube was passed through a fluororesin-made gas washing bottle filled with ice water and cooled in an ice bath, so as to absorb unreacted hydrogen fluoride and hydrogen chloride and trap the reaction product. The reaction product was analyzed by gas chromatography. The analysis results of changes in reaction yield over time are shown in FIG. 3.

Figure 3:
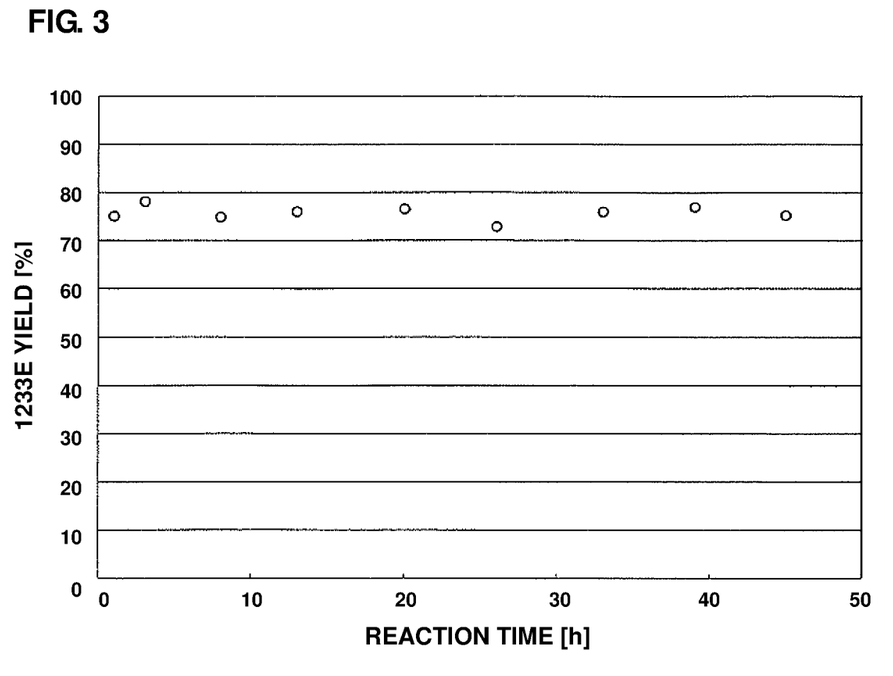

As is seen from FIG. 3, the catalytic activity of the fluorinated alumina catalyst was maintained at a favorable level over 45 hours in the present invention.

DESCRIPTION OF REFERENCE NUMERALS

1: Valve
2: Valve
3: Valve
4: Valve
5: Valve
6: Valve
7: Valve
8: Valve
10: Liquid-phase reaction chamber
11: Pipe
13: Pipe
15: Pipe
17: Pipe
30: Condenser
31: Pipe
35: Condenser
36: Pipe
50: Tank 70: Tank
71: Pipe
90: Gas-phase reaction column
91: Pipe
93: Pipe
95: Pipe
100: Production device

The invention claimed is:

1. A production method of trans-1-chloro-3,3,3-trifluoropropene, comprising reacting a raw reactant material containing a plurality of halogenated $C_3$ hydrocarbon compounds represented by the following general formula (1) with hydrogen fluoride in a gas phase in the presence of a solid catalyst and chlorine $$C_3H_XCl_YF_Z \qquad (1)$$

wherein X is 2 or 3; when X=2, Y is an integer of 1 to 4, Z is an integer of 0 to 3, and Y+Z=4; and, when X=3, Y is an integer of 1 to 5, Z is an integer of 0 to 4, and Y+Z=5; provided that the general formula (1) represents any halogenated $C_3$ hydrocarbon compound other than trans-1-chloro-3,3,3-trifluoropropene, wherein, in the reacting, the raw reactant material further comprises a $C_3$ hydrocarbon compound represented by the following general formula (2)

$$C_3H_VF_W \qquad (2)$$

wherein, when V+W=8, V is an integer of 0 to 8; when V+W=6, V is an integer of 0 to 6; and, when V+W=4, V is an integer of 0 to 4.

2. The production method according to claim 1, wherein the solid catalyst is a metal fluoride containing at least one kind of metal selected from the group consisting of aluminum, chromium, titanium, manganese, iron, nickel, cobalt, copper, magnesium, zirconium, molybdenum, zinc, tin, lanthanum, niobium, tantalum and antimony.

3. The production method according to claim 1, wherein the plurality of halogenated $C_3$ hydrocarbon compounds are selected from the group consisting of 1,1,1,3,3-pentachloropropane, 1,1,3,3-tetrachloropropene, 1,3,3,3-tetrachloropropane, 1,1,3,3-tetrachloro-1-fluoropropane, 1,1,1,3-tetrachloro-3-fluoropropane, 1,3,3-trichloro-3-fluoropropene, 1,3,3-trichloro-1-fluoropropene, 3,3,3-trichloro-1-fluoropropene, 1,1,3-trichloro-3-fluoropropene, 1,3,3-trichloro-1,1-difluoropropane, 1,1,3-trichloro-1,3-difluoropropane, 1,1,1-trichloro-3,3-difluoropropane, 1,3-dichloro-3,3-difluoropropene, 3,3-dichloro-1,3-difluoropropene, 3,3-dichloro-1,1-difluoropropene, 1,3-dichloro-1,3-difluoropropene, 1,1-dichloro-3,3-difluoropropane, cis-1-chloro-3,3,3-trifluoropropene, 3-chloro-1,1,3-trifluoropropene, 3-chloro-1,3,3-trifluoropropene, 1-chloro-1,3,3-trifluoropropene, 3,3-dichloro-1,1,1-trifluoropropane, 1,3-dichloro-1,1,3-trifluoropropane, 1,1-dichloro-1,3,3-trifluoropropane, 1-chloro-1,1,3,3-tetrafluoropropane and 3-chloro-1,1,1,3-tetrafluoropropane.

4. The production method according to claim 1, wherein the reacting is performed at a temperature of 100° C. to 400° C.

5. A production method of trans-1-chloro-3,3,3-trifluoropropene, comprising reacting a raw reactant material containing a plurality of halogenated hydrocarbon compounds selected from the group consisting of 1,1,3,3-tetrachloro-1-fluoropropane, 1,1,1,3,3-pentachloropropane and 1,3,3-trichloro-1,1-difluoropropane with hydrogen fluoride at a temperature of 100° C. to 400° C. in a gas phase in the presence of a solid catalyst and chlorine, wherein, in the reacting, the raw reactant material further comprises a $C_3$ hydrocarbon compound represented by the following general formula (2)

$$C_3H_VF_W \qquad (2)$$

wherein, when V+W=8, V is an integer of 0 to 8; when V+W=6, V is an integer of 0 to 6; and, when V+W=4, V is an integer of 0 to 4.

6. A production method of trans-1-chloro-3,3,3-trifluoropropene, comprising the following steps:
(A) reacting 1,1,1,3,3-pentachloropropane with hydrogen fluoride, thereby obtaining an intermediate product;
(B) forming trans-1-chloro-3,3,3-trifluoropropene by using the intermediate product obtained in the step (A) as a raw reactant material comprising a plurality of halogenated $C_3$ hydrocarbon compounds including cis-1-chloro-3,3,3-trifluoropropene and reacting the raw reactant material with hydrogen fluoride at a temperature of 100° C. to 400° C. in a gas phase in the presence of a solid catalyst and chlorine.

7. The production method according to claim 6, wherein, in the step (B), the raw reactant material further comprises a $C_3$ hydrocarbon compound represented by the following general formula (2)

$$C_3H_VF_W \qquad (2)$$

wherein, when V+W=8, V is an integer of 0 to 8; when V+W=6, V is an integer of 0 to 6; and, when V+W=4, V is an integer of 0 to 4.

8. The production method according to claim 7, wherein, in the step (A), the reacting is performed in a liquid phase in the absence of a catalyst, and
wherein the production method further comprises:
recovering, from the step (A), a reaction product gas containing trans-1-chloro-3,3,3-trifluoropropene and a reaction solution; and
using, in the step (B), the intermediate product contained in the reaction solution as the raw reactant material.

9. The production method according to claim 8,
wherein the 1,1,1,3,3-pentachloropropane and the hydrogen fluoride are continuously or intermittently introduced into the step (A), and
wherein the reaction product gas and the reaction solution are continuously or intermittently recovered.

10. The production method according to claim 7, wherein the intermediate product is at least one selected from the group consisting of 1,1,3,3-tetrachloropropene, 1,3,3,3-tetrachloropropane, 1,1,3,3-tetrachloro-1-fluoropropane, 1,1,1,3-tetrachloro-3-fluoropropane, 1,3,3-trichloro-3-fluoropropene, 1,3,3-trichloro-1-fluoropropene, 3,3,3-trichloro-1-fluoropropene, 1,1,3-trichloro-3-fluoropropene, 1,3,3-trichloro-1,1-difluoropropane, 1,1,3-trichloro-1,3-difluoropropane, 1,1,1-trichloro-3,3-difluoropropane, 1,3-dichloro-3,3-difluoropropene, 3,3-dichloro-1,3-difluoropropene, 3,3-dichloro-1,1-difluoropropene, 1,3-dichloro-1,3-difluoropropene, 1,1-dichloro-3,3-difluoropropane, cis-1-chloro-3,3,3-trifluoropropene, 3-chloro-1,1,3-trifluoropropene, 3-chloro-1,3,3-trifluoropropene, 1-chloro-1,3,3-trifluoropropene, 3,3-dichloro-1,1,1-trifluoropropane, 1,3-dichloro-1,1,3-trifluoropropane, 1,1-dichloro-1,3,3-trifluoropropane, 1-chloro-1,1,3,3-tetrafluoropropane and 3-chloro-1,1,1,3-tetrafluoropropane.

11. The production method according to claim 7, wherein the intermediate product comprises at least 1,3,3-trichloro-1,1-difluoropropane.

12. The production method according to claim 7, wherein, in the step (B), the reacting is performed at a temperature of 150° C. to 300° C.

13. The production method according to claim 7, further comprising recovering and using unreacted intermediate product in the step (B).

14. The production method according to claim 7, wherein the cis-1-chloro-3,3,3-trifluoropropene is formed along with the trans-1-chloro-3,3,3-trifluoropropene in the step (B).

15. The production method according to claim 6,
wherein, in the step (A), the reacting is performed in a liquid phase in the absence of a catalyst, and
wherein the production method further comprises:
recovering, from the step (A), a reaction product gas containing trans-1-chloro-3,3,3-trifluoropropene and a reaction solution; and
using, in the step (B), the intermediate product contained in the reaction solution as the raw reactant material.

16. The production method according to claim 15,
wherein the 1,1,1,3,3-pentachloropropane and the hydrogen fluoride are continuously or intermittently introduced into the step (A), and
wherein the reaction product gas and the reaction solution are continuously or intermittently recovered.

17. The production method according to claim 6,
wherein the intermediate product is at least one selected from the group consisting of 1,1,3,3-tetrachloropropene, 1,3,3,3-tetrachloropropane, 1,1,3,3-tetrachloro-1-fluoropropane, 1,1,1,3-tetrachloro-3-fluoropropane, 1,3,3-trichloro-3-fluoropropene, 1,3,3-trichloro-1-fluoropropene, 3,3,3-trichloro-1-fluoropropene, 1,1,3-trichloro-3-fluoropropene, 1,3,3-trichloro-1,1-difluoropropane, 1,1,3-trichloro-1,3-difluoropropane, 1,1,1-trichloro-3,3-difluoropropane, 1,3-dichloro-3,3-difluoropropene, 3,3-dichloro-1,3-difluoropropene, 3,3-dichloro-1,1-difluoropropene, 1,3-dichloro-1,3-difluoropropene, 1,1-dichloro-3,3-difluoropropene, 1,1-dichloro-3,3-difluoropropane, cis-1-chloro-3,3,3-trifluoropropene, 3-chloro-1,1,3-trifluoropropene, 3-chloro-1,3,3-trifluoropropene, 1-chloro-1,3,3-trifluoropropene, 3,3-dichloro-1,1,1-trifluoropropane, 1,3-dichloro-1,1,3-trifluoropropane, 1,1-dichloro-1,3,3-trifluoropropane, 1-chloro-1,1,3,3-tetrafluoropropane and 3-chloro-1,1,1,3-tetrafluoropropane.

18. The production method according to claim 6,
wherein the intermediate product contains at least 1,3,3-trichloro-1,1-difluoropropane.

19. The production method according to claim 6,
wherein, in the step (B), the reacting is performed at a temperature of 150° C. to 300° C.

20. The production method according to claim 6, further comprising recovering and using unreacted intermediate product in the step (B).

21. The production method according to claim 6, wherein the cis-1-chloro-3,3,3-trifluoropropene is formed along with the trans-1-chloro-3,3,3-trifluoropropene in the step (B).

22. The production method according to claim 21,
wherein the cis-1-chloro-3,3,3-trifluoropropene is used as the raw reactant material in the step (B).

23. The production method according to claim 21, further comprising converting the cis-1-chloro-3,3,3-trifluoropropene to trans-1-chloro-3,3,3-trifluoropropene by heating at a temperature of 100° C. to 400° C.

* * * * *